(12) United States Patent
Schnell et al.

(10) Patent No.: US 6,808,892 B1
(45) Date of Patent: Oct. 26, 2004

(54) METHOD FOR IDENTIFYING INHIBITORS OF IPC SYNTHASE

(75) Inventors: Norbert F. Schnell, Cheshire (GB); Jini S Chavada, Cheshire (GB)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/831,290

(22) PCT Filed: Nov. 12, 1999

(86) PCT No.: PCT/GB99/03789

§ 371 (c)(1),
(2), (4) Date: May 8, 2001

(87) PCT Pub. No.: WO00/29590

PCT Pub. Date: May 25, 2000

(30) Foreign Application Priority Data

Nov. 17, 1998 (GB) .............................. 9825055

(51) Int. Cl.$^7$ ............................ C12Q 1/18; C12Q 1/02; C12N 1/15
(52) U.S. Cl. ....................... 435/32; 435/254.11; 435/29
(58) Field of Search .............................. 435/254.11, 29, 435/32

(56) References Cited

U.S. PATENT DOCUMENTS 5,667,986 A  9/1997 Goodey et al. ............ 435/69.1

FOREIGN PATENT DOCUMENTS

| AU | 63129/94 | 12/1994 |
|----|----------|---------|
| EP | 0424117 B1 | 4/1991 |
| EP | 0644262 A2 | 3/1995 |
| WO | WO-96/38573 A1 | 12/1996 |

OTHER PUBLICATIONS

Nagiec et al. Sphingolipid synthesis as a target for antifungal drugs. Complementation of the inositol phosphorylceramide synthase defect in a mutant strain of Saccharomyces cerevisiae by the AUR1 gene. J Biol Chem. Apr. 11, 1997;271(15):9809–17.*

* cited by examiner

*Primary Examiner*—David Guzo
*Assistant Examiner*—Daniel M. Sullivan
(74) *Attorney, Agent, or Firm*—Ropes & Gray LLP

(57) ABSTRACT

A screening assay for identifying a selective IPC synthase inhibitor which assay comprises contacting a test compound with engineered cells whose capability to synthesize sphingolipids depends on the addition of exogenous phytosphingosine and which are capable of sustained growth via compensatory phospholipids, adding phytosphingosine, and determining IPC synthase inhibition by the test compound by reference to any cell growth inhibition. Engineered cells for use in the assay.

8 Claims, 2 Drawing Sheets

SEQUENCE LISTING

<160> NUMBER OF SEQ ID NOS: 6

<210> SEQ ID NO 1
<211> LENGTH: 82
<212> TYPE: DNA
<213> ORGANISM: Artificial Sequence
<220> FEATURE:

-continued

<223> OTHER INFORMATION: Description of Artificial Sequence: 5' PCR
      primer for creation of LCB1 deletion

<400> SEQUENCE: 1
gcaatggcac acatcccaga ggttttaccc aaatcaatac cgattccggc atttattgca    60
gctgaagctt cgtacgctgc ag                                             82

<210> SEQ ID NO 2
<211> LENGTH: 75
<212> TYPE: DNA
<213> ORGANISM: Artificial Sequence
<220> FEATURE:
<223> OTHER INFORMATION: Description of Artificial Sequence: 3' PCR
      primer for creation of LCB1 deletion

<400> SEQUENCE: 2
ctatttttat ttattagatt cttggcaaca ggcaaggatg gactgcttga cccgcatagg    60
ccactagtgg atctg                                                     75

<210> SEQ ID NO 3
<211> LENGTH: 144
<212> TYPE: DNA
<213> ORGANISM: Artificial Sequence
<220> FEATURE:
<223> OTHER INFORMATION: Description of Artificial Sequence: 5' PCR
      primer for creation of SLC1-1

<400> SEQUENCE: 3
cgcggatcca tgagtgtgat aggtaggttc ttgtattact tgaggtccgt gttggtcgta    60
ctggcgcttg caggctgtgg cttttacggt gtaatcgcct ctatcctgtg cacgttaatc   120
ggtaagcaac atttggctct gtgg                                          144

<210> SEQ ID NO 4
<211> LENGTH: 37
<212> TYPE: DNA
<213> ORGANISM: Artificial Sequence
<220> FEATURE:
<223> OTHER INFORMATION: Description of Artificial Sequence: 3' PCR
      primer for creation of SLC1-1

<400> SEQUENCE: 4
acatgcatgc ttaatgcatc ttttttacag atgaacc                             37

<210> SEQ ID NO 5
<211> LENGTH: 48
<212> TYPE: DNA
<213> ORGANISM: Artificial Sequence
<220> FEATURE:
<223> OTHER INFORMATION: Description of Artificial Sequence: 5' PCR
      primer for creation of GPD3 promoter

<400> SEQUENCE: 5
cccaagcttg ccggcactag ttcgagttta tcattatcaa tactcgcc                 48

<210> SEQ ID NO 6
<211> LENGTH: 31
<212> TYPE: DNA
<213> ORGANISM: Artificial Sequence
<220> FEATURE:

-continued

```
<223> OTHER INFORMATION: Description of Artificial Sequence: 3' PCR
      primer for creation of GPD3 promoter

<400> SEQUENCE: 6
gtaagcttta ttcgaaacta agttcttggt g                                    31
```

METHOD FOR IDENTIFYING INHIBITORS OF IPC SYNTHASE

Figure 1A:
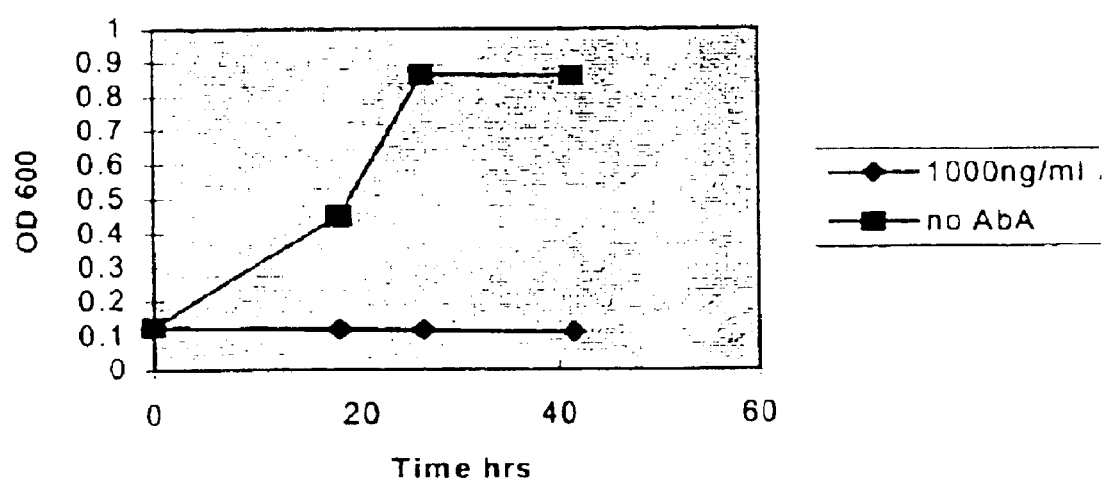

This application is the National Phase of International Application PCT/GB99/03789 filed Nov. 12, 1999 which designated the U.S. and that International Application was published under PCT Article 21(2) in English.

The present invention relates to a cell-based screen for inhibitors of fungal inositolphosphoryl-ceramide (IPC) synthase, an important antifungal target.

Inhibitors of fungal IPC synthase are potent and selective antifungal agents for example Aureobasidin, Khafrefungin and Rustmicin) as identified by several research groups and pharmaceutical companies.

However, all such compounds are natural products that are difficult to produce, handle and administer to a patient (for example, they may have unsuitable pharmacokinetics). Therefore it is highly desirable to obtain other novel chemical compounds selectively inhibiting the same target (a fungal IPC synthase) but without the intrinsic disadvantages displayed by the currently known inhibitors. Screening for such novel chemicals as well as optimisation of already available "leads" (ie. optimisation of a known inhibitor in a structure-based design or lead optimisation) will require an assay for IPC synthase activity that can be performed at a sufficiently high throughput.

All currently available biochemical assays for IPC synthase are involved and very labour-intensive.

Nagiec et al (Journal of Biological Chemistry, Vol 272 No 15, pp 9809–9817 (1997))) describe the complementation of an IPC synthase gene defect in a mutant strain of S. Cerevisiae by the AUR1 gene. The mutant strain has a deletion of the LCB1 gene and a point mutation that creates the suppressor gene SLC1-1. The lcb1 mutation prevents sphingolipid synthesis and the SLC-1-1 gene enables the cells to make phospholipids and remain viable. (Use of capital letters implies a functional gene or a gain of function mutation such as SLC1-1 whereas small letters indicate a non functional allele such as lcb1). Using this the authors were able to isolate a mutant strain defective in IPC synthase and to isolate a gene AUR1 which complemented the IPC synthase defect and restored IPC synthase activity. The authors conclude that IPC synthase is the target for antifungal agents such as aureobasidin. They postulate that it should be possible to develop high throughput screens to identify new inhibitors of IPC synthase to combat fungal diseases.

However we have found that whilst a similar strain of S. cerevisiae (lcb1/SLC1-1) is viable, the strain grows very poorly and is extremely sensitive to any environmental influences such as for example freezing. This strain is simply not robust enough for screening purposes.

We now provide a robust cell-based assay for identifying selective IPC synthase inhibitors. This assay is based on our development of an S. cerevisiae strain wherein the production of compensatory phospholipids is enhanced.

Therefore in a first aspect of the present invention we provide a screening assay for identifying a selective IPC synthase inhibitor which assay comprises contacting a test compound with engineered cells whose capability to synthesize sphingolipids depends on the addition of exogenous phytosphingosine and which are capable of sustained growth via compensatory phospholipids, adding phytosphingosine, and determining IPC synthase inhibition by the test compound by reference to any cell growth inhibition.

Any convenient host cell strain may be used provided that it can function as a host for a fungal IPC synthase gene. Convenient hosts include fungi that are manipulatable C) genetically such as S. cerevisiae but also others such as Candida albicans, Candida glabrata, Aspergillus sp. or Schizosaccharomyces pombe. Convenient sources for the AUR1 gene are pathogenic (also phytopathogenic) fungi as outlined above and others such as Ashbya sp., Fusarium sp., Trichoderma sp., Cryptococci, Blastomyces, and Histoplasma.

Whilst we do not wish to be bound by theoretical considerations the compensatory phospholipids are believed to be novel glycerophospholipids that may compensate for one or more functions of sphingolipids essential for vegetative growth (Lester et al, J. Biol. Chem., 1993, 268, 845–856).

In a further aspect of the invention we provide engineered cells whose capability to synthesize sphingolipids depends on the addition of exogenous phytosphingosine and which are capable of sustained growth via compensatory phospholipids By "sustained growth" we mean no significant decrease of viable cell counts during a growth period (ie. cell-death is negligible compared to cell growth). The strain also has to be capable of one or more of the following: being stored for prolonged periods, for example up to three or six months or longer; storage in liquid medium; or capable of being frozen and revived. The engineered cells of the invention are capable and robust enough for routine use in high throughput assay procedures. In general they will have generation times compatible with growth assays (ie. not more than 4 hours per doubling) and final optical densities reached of more than 4 OD (at 600 nm and 1 cm path length). These parameters allow complete assessment of a host strain's growth within less than 30 hours.

A convenient host strain for use in the assay methods of the invention is an lcb1/SLC1-1 strain. More conveniently it will include a selection marker, for example the lcb1 gene may be directly replaced by an amino acid biosynthetic gene (such as LEU2, TRP1 or HIS3) or antibiotic resistance such as Geneticin (G418).

Adapting host cells for sustained growth is for example achieved by enhancing expression of the compensatory mutant SLC1-1 allele. We have surprisingly found that can be achieved by cloning the SLC1-1 gene onto a multi-copy plasmid (pYES2-LEU2d-GPD3-SLC1-1=pNS149) under control of the glyceraldehyde 3-phosphate dehydrogenase promoter. Use of a multi-copy pGPD-SLC1-1 promoter/gene construct yielded a strain with much improved growth characteristics, improved growth rate, final optical density and resistance to freezing. In summary it provided for the first time a host strain which is robust enough for screening purposes.

The GPD3 is an example of a very strong constitutive promoter in S. cerevisiae. Other glycolytic enzymes such as Phosphoglycerate Kinase (PGK), Enolase 1 (ENO), Pyruvate Kinase (PYK) and Fructose-Bisphosphate Aldolase II FBA are convenient sources of other such promoters.

Therefore in a further aspect of the invention we provide an engineered host strain S. cerevisiae (lcb1/pGPD-SLC1-1).

The invention will now be illustrated but not limited by reference to the following Examples and Figures:

EXAMPLES

Example 1

Construction of the IPC Synthase Screening Strain (lcb1::kanMX, pNS149 (pGPD3-SLC1-1))

(i) Generation of a LCB1 deletion strain

As LCB1 is an essential gene, only one allele of a diploid cell can be deleted without loss of survival. Added phytosphingosine can, however, substitute for an intact LCB1 gene. Technically, one LCB1 allele of a diploid S. cerevisiae strain (JK9-3daa—Kunz, J. et al, Cell, 1993, 73, 585–596) was disrupted using the kanamycin resistance cassette as described by Wach et al, Yeast, 1996, 12, 259–265.
PCR primers used to create the LCB1 deletion (lcb1::kanMX)
5' Primer:
GCAATGGCACACATCCCAGAGGTTTTAC-CCAAATCAATACCGATTCCGGCATTTATT GCAGCTGAAGCTTCGTACGCTGCAG (SEQ ID NO: 1)
3' Primer:
CTATTTTTATTTATTAGATTCTTGGCAACAGG-CAAGGATGGACTGCTTGACCCGCAT AGGCCAC-TAGTGGATCTG (SEQ ID NO: 2)

Disruption of LCB1 and its replacement by kanMX was verified by PCR (using primers 5' of the deleted region directed towards the gene and within kanMX facing towards the promoter). Sporulation of the heterozygous diploid (LCB1/lcb1::KanMX) and tetrad dissection yields 2 kanamycin-sensitive colonies per tetrad when grown on YPD (Sherman et al, Methods in Yeast Genetics, 1986, Cold Spring Harbor Laboratory Press, Cold Spring Harbor N.Y. media) without phytosphingosine, however if the ascus is dissected on media containing 10 mM phytosphingosine this results in 4 colonies per tetrad, two of which are resistant to kanamycin (and therefore are lcb1::kanMX).

(ii) Generation of a SLC1-1 allele cloned into a multi-copy plasmid

The dominant SLC1-1 allele was generated from the wildtype allele by PCR regenerating the sequence as described by Nagiec et al. (op cit). The mutant SLC1-1 allele differs from the wildtype allele by a single nucleotide which changes Glutamine 44 in the wild-type protein to Leucine in the suppressor protein. According to the literature (Nagiec et al, op cit) this mutation should rescue the lcb1::kanMX strain, allowing growth on media without added phytosphingosine.

The SLC1-1 was amplified from genomic DNA by PCR (creating the point mutation via a mismatch in the 5' primer) and cloned into expression plasmids (eg pYES2-Leu2 (Invitrogen), modified by an inserted Leu2 selection marker=pNS144) using BamHI (5') and SphI (3') as insertion sites (to give pNS145). After transformation (5) into lcb1::kanMX (3), (selection SGal-leucine, no phytosphingosine added) microcolonies were established after 12 days of incubation proving and confirming the suppressing function of SLC1-1. However, the viability of these transformants was extremely poor and they were not maintainable in liquid culture. Establishment of frozen stocks from the colonies also failed. A similar phenotype was also observed if the homologous SLC1 promoter was used instead of Gal1 (pNS148).

Primers to generate SLC1-1 by PCR. Restriction sites are shown in bold. The point mutation generating Leu 44 is shown underlined in italics SLC1-1 5'
CGCGGATCCATGAGTGTGATAGGTAGGT-TCTTGTATTACTTGAGGTCCGTGTTGGTC GTACTGGCGCTTGCAGGCTGTGGCTTT-TACGGTGTAATCGCCTCTATCCTGTGCACGT TAATCGGTAAGCAACATTTGGCTCTGTGG (SEQ ID NO: 3)
SLC1-1 3'
ACATGCATGCTTAATGCATCTTTTTTACAGATG-AACC (SEQ ID NO: 4)

(iii) Generation of a GPD3-driven SLC1-1 allele

We postulated that the poor viability of the lcb1::kanMX pNS145 strain might be due to insufficient expression of SLC1-1, so increased expression was attempted. We placed the SLC1-1 gene under control of the glyceraldehyde-3-phosphate dehydrogenase GPD3 (=TDH3), promoter (Norbeck et al, Yeast, 1997, 16, 1519–1534).

The GPD3 promoter was amplified from S. cerevisiae chromosomal DNA by PCR and inserted into a HinDIII site of PNS145 (just 5' of the SLC1-1 start ATG) to create plasmid pNS149 which is a further independent aspect of the invention.

PCR primers generating the GPD3 promoter. Restriction sites are shown in bold

PGPD5'
CCCAAGCTTGCCGGCACTAGTTCGAOTT-TATCATFATCAATACTCGCC (SEQ ID NO: 5)
pGPD 3'
GTAAGCTTTATTCGAAACTAAGTTCTTGGTG (SEQ ID NO: 6)

Transformation (Ito et al, J. Bacteriology, 1983, 153, 163–168) of pNS149 into lcb1::kanMX (see 2. above) yielded readily viable colonies, that also grew very well in liquid culture and were able to recover from freeze-storage.

Example 2

The IPC Synthase Screen

Figure 1B:
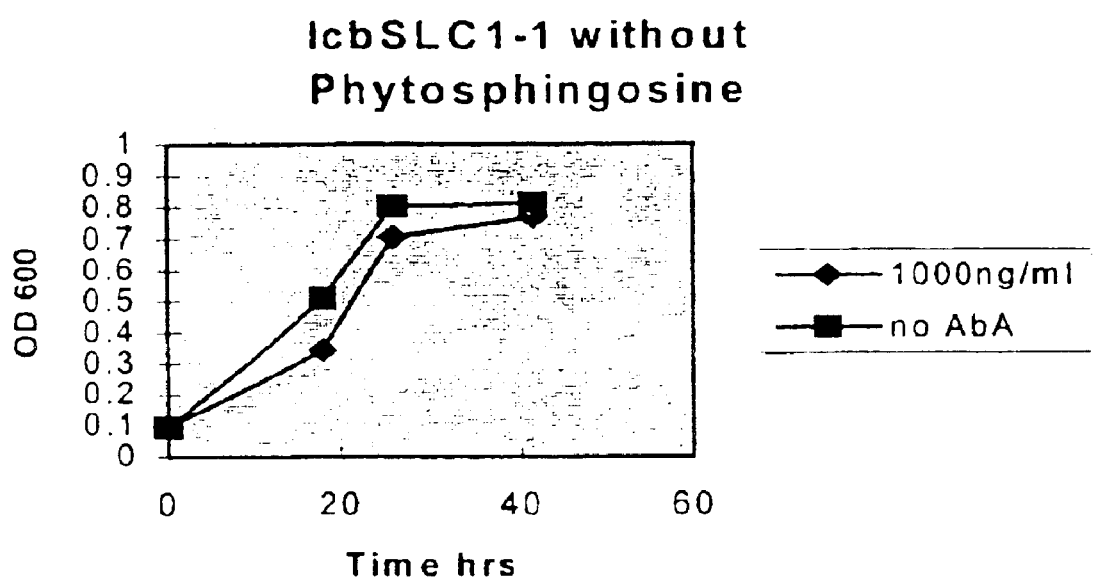

The utility of the lcb1::kanMX pNS149 strain to identify inhibitors of IPC synthase was evaluated using aureobasidinA as a test compound. The lcb1::kanMX pNS149 strain is a further independent aspect of the invention. As shown in FIG. 1, the test compound could be readily identified, as predicted. Inhibition by aureobasidinA was very pronounced in the presence of phytosphingosine but absent if no phytosphingosine was added.

FIG. 1a

Inhibition of growth by aureobasidinA in strain lcb1::kanMX, pNS149 with added phytosphingosine.

FIG. 1b

Inhibition of growth by aureobasidinA in strain lcb1::kanMX, pNS149 without added phytosphingosine.

What is claimed is:

1. A screening assay for identifying a selective IPC synthase inhibitor which assay comprises contacting a test compound with engineered fungal cells whose capability to synthesize sphingolipids depends on the addition of exogenous phytosphingosine and which are capable of sustained growth via compensatory phospholipids, adding phytosphingosine, and determining IPC synthase inhibition by the test compound by reference to any cell growth inhibition, wherein the cells comprise an lcb1 allele and overexpress an SLC1-1 gene that is operably linked to a heterologous promoter.

2. Engineered cells whose capability to synthesize sphingolipids depends on the addition of exogenous phytosphingosine and which are capable of sustained growth via compensatory phospholipids, wherein the cells comprise an lcb1 allele and overexpress an SLC1-1 gene that is operably linked to a heterologous promoter.

3. Engineered cells whose capability to synthesize sphingolipids depends on the addition of exogenous phytosphingosine and which are capable of sustained growth via compensatory phospholipids, wherein the host strain is an lcb1/SLC1-1 strain and wherein the SLC1-1 gene is under the control of the glyceraldehyde-3-phosphate dehydrogenase (GPD3) promoter.

4. *S. cerevisiae* yeast cells comprising an lcb1 allele and overexpressing an SLC1 gene that is operably linked to a heterologous promoter, wherein the promoter is glyceraldehyde-3-phosphate dehydrogenase (GPD3).

5. The cells of claim 2, wherein the promoter is selected from the phosphoglycerate kinase (PGK) promoter, the enolase 1 (ENO) promoter, the pyruvate kinase (PYK) promoter, and the fructose-bisphosphate aldolase II (FBA) promoter.

6. The assay of claim 1, wherein the promoter is selected from the phosphoglycerate kinase (PGK) promoter, the enolase 1 (ENO) promoter, the pyruvate kinase (PYK) promoter, and the fructose-bisphosphate aldolase II (FBA) promoter.

7. The assay of claim 1, wherein the SLC1-1 gene is under the control of the glyceraldehyde-3-phosphate dehydrogenase (GPD3) promoter.

8. The assay of claim 7, wherein the cells are *S. cerevisiae* yeast cells.

\* \* \* \* \*

UNITED STATES PATENT AND TRADEMARK OFFICE
CERTIFICATE OF CORRECTION

PATENT NO.    : 6,808,892 B1
DATED         : October 26, 2004
INVENTOR(S)   : Schnell et al.

It is certified that error appears in the above-identified patent and that said Letters Patent is hereby corrected as shown below:

Column 1,
Line 63, delete "C)".

Column 8,
Line 14, delete "SLC1" and instead insert -- SLC1-1 --.

Signed and Sealed this

First Day of March, 2005

JON W. DUDAS
*Director of the United States Patent and Trademark Office*